United States Patent  
Tomlinson (10) Patent No.: US 8,152,181 B2  
(45) Date of Patent: Apr. 10, 2012

(54) MOBILITY FRAME (75) Inventor: Leslie Tomlinson, Cooloongup (AU)

(73) Assignee: About Time Technologies Pty. Ltd. (AU)

( * ) Notice: Subject to any disclaimer, the term of this patent is extended or adjusted under 35 U.S.C. 154(b) by 225 days.

(21) Appl. No.: 12/094,583

(22) PCT Filed: Nov. 21, 2006

(86) PCT No.: PCT/AU2006/001756  
§ 371 (c)(1),  
(2), (4) Date: Sep. 15, 2008

(87) PCT Pub. No.: WO2007/056830  
PCT Pub. Date: May 24, 2007

(65) Prior Publication Data  
US 2009/0058033 A1 Mar. 5, 2009

(30) Foreign Application Priority Data

Nov. 21, 2005 (AU) .............................. 2005906443  
Apr. 12, 2006 (AU) .............................. 2006901928

(51) Int. Cl.  
B62B 3/00 (2006.01)  
B62B 3/02 (2006.01)

(52) U.S. Cl. ............. 280/47.34; 280/47.35; 280/47.371; 280/47.41; 280/79.11; 280/79.3; 280/79.6

(58) Field of Classification Search .................. 280/638, 280/35, 639, 655.1, 47.34, 47.35, 47.371, 280/79.11, 79.6, 79.7, 87.041; 248/163.1, 248/164, 431, 176.1  
See application file for complete search history.

(56) References Cited

U.S. PATENT DOCUMENTS 4,225,104 A * 9/1980 Larson ........................ 248/125.8  
4,332,378 A 6/1982 Pryor  
4,905,944 A 3/1990 Jost et al.  
5,344,169 A * 9/1994 Pryor et al. .................. 280/79.3  
5,411,044 A * 5/1995 Andolfi ........................... 135/66  
(Continued)

FOREIGN PATENT DOCUMENTS  
AU 303810 11/2005  
(Continued)

OTHER PUBLICATIONS

Kerry Equipment Australia: Mobile Intravenous Stand with Syringe Pump Mount Facility product information, http://www.kerryequipment.com.au/products.php?id=206, May 20, 2008, pp. 1-2.

(Continued)

Primary Examiner — J. Allen Shriver, II  
Assistant Examiner — Bryan Evans  
(74) Attorney, Agent, or Firm — Marger Johnson & McCollom PC (57) ABSTRACT A mobility frame (10) comprising: a multi-wheeled base (11), an upstanding support (13) having a substantially upright lower portion (17) attached to the base (11), an oblique portion (27) disposed at a height from the base (11), the oblique portion (27) extending obliquely upwardly from the lower portion (17), an upper portion (29) extending substantially upwardly from the oblique portion (27); and at least one handle (35) for steering the mobility frame (10) and/or for allowing a user to support them-self on the mobility frame (10).

25 Claims, 10 Drawing Sheets

U.S. PATENT DOCUMENTS

| | | | | |
|---|---|---|---|---|
| 5,671,765 | A * | 9/1997 | Hagberg, Jr. | 135/68 |
| 6,390,311 | B1 * | 5/2002 | Belokin | 211/204 |
| 2005/0116126 | A1 * | 6/2005 | Ugent et al. | 248/129 |
| 2005/0183298 | A1 * | 8/2005 | Cohen et al. | 40/308 |
| 2005/0275178 | A1 * | 12/2005 | Huesdash et al. | 280/47.35 |
| 2006/0016466 | A1 * | 1/2006 | Carroll | 135/67 |

FOREIGN PATENT DOCUMENTS

| | | |
|---|---|---|
| DE | 20005527 | 7/2000 |
| DE | 20219431 | 4/2003 |
| FR | 2667239 | 4/1992 |
| WO | WO98/07402 | 2/1998 |
| WO | WO2004/101034 | 11/2004 |

OTHER PUBLICATIONS

Premier Medical Products Co., Offset IV Stand product information, http://premieremedical.safeshopper.com/100/790.htm?81, Mar. 10, 2006, p. 1.

* cited by examiner

MOBILITY FRAME

FIELD OF THE INVENTION

This invention relates to an intravenous mobility frame with medical apparatus support.

BACKGROUND OF THE INVENTION

Intravenous support poles are used in hospitals and like locations to support fluids, monitoring devices and pumps and the like which are used for delivering and controlling the delivery of fluids to patients. In the most basic form intravenous poles are utilised to support bags containing intravenous fluids at a suitable height above the ground (which is usually approximately 1.9 meters) to allow for the gravitational feed of a fluid into the patient. In other occasions the fluids are delivered to the patient by means of a pump and therefore the fluids do not need to be located at specific height above the patient. It is usual to locate the pumps at a position at which they can be readily observed by medical staff which requires them to be put at a position which will approximate eye level to avoid the need for the medical staff to have to bend every time they are required to take a reading or observe the operational status of the apparatus.

Intravenous poles of the form as described above present a significant problem in that because of the high degree of mass located towards the upper end of the intravenous pole they have a high centre of gravity and become inherently unstable. Therefore when a patient is required to move from the bed or is in walking phase, they are required to also move the intravenous pole with all of the associated equipment which is mounted to the pole. In the event that the pole is knocked or the patient loses momentary stability very minimal effort is required in order for the intravenous pole to tip over. In addition, because the only means of support engaging the pole comprises the central pole itself, as the pole is moved over the ground it is often the case that one or more of the castors becomes jammed or engage with an item on the floor which causes the pole to rotate about its central axis and/or to begin to tip.

DISCLOSURE OF THE INVENTION

In one aspect, the present invention provides a mobility frame comprising:
   a multi-wheeled base,
   an upstanding support having:
      a substantially upright lower portion attached to the base,
      an oblique portion disposed at a height from the base, the oblique portion extending obliquely upwardly from the lower portion,
      an upper portion extending substantially upwardly from the oblique portion; and
   at least one handle for steering the mobility frame and/or for allowing a user to support them self on the mobility frame.

Preferably, the lower portion is substantially aligned with the upright central axis of the base. Preferably, the height of the oblique portion is such that monitoring devices attached thereto can be viewed by a user or carer standing next to the mobility frame. The oblique portion is preferably attached to a lateral arm of the support and offset from the lower portion, such that the oblique portion and upper portion are located to a side of a central axis of the mobility frame to substantially prevent same from blocking a user's forward direction view.

Preferably, the upper portion is angled in the rearward direction such that loads attached to the upper portion are located closer to a central axis of the mobility frame.

The base is preferably defined by a first arm extending radially from the upstanding support and a pair of second arms which are in an opposed relation to the first arm and divergent with respect to each other, the first arm and second arms each being supported from the ground by a wheel. The spacing between the wheels of the second arms is preferably sufficient to enable a person to engage the handle(s) and stand between the second arms. The first arm preferably extends forwardly beyond the central axis of the upper portion of the support to provide stability. The first and second arms are preferably divergently downwardly with respect to the central axis. The base preferably includes two first arms which are in opposed relation to the second arms, the first arms each being supported from the ground by a wheel. The first arms are preferably parallel to each other, and at least one arm preferably includes a means for supporting a cylinder tank thereon.

Preferably, the mobility frame is provided with a pair of handles, each handle extending from a lateral arm attached to the support, the handles extending in opposed relation to the oblique portion and spaced equi-distant to each side of a central axis of the frame. The handles are preferably adjustable in height. Preferably, each lateral arm has a vertical tubular portion with a clamp, each handle comprises a vertical portion slidingly received in the tubular portion and a horizontal portion having a grip, such that the height of the grips can be adjusted by moving the vertical portions vertically relative to the lateral arms and then locking the desired grip height via the clamp. Preferably, a curved portion connects the vertical and horizontal portions of the grip.

The handles can include forearm supports for supporting the user's forearms. The forearm supports can include an elongate horizontal concave portion which is padded at its top surface, the front end of the concave portion having a vertical grip. The handles are preferably located above the space defined between the rear wheels.

The oblique portion preferably extends from the upper end of the lower portion. The upper portion preferably extends from the upper end of the oblique portion. The oblique portion is preferably substantially intermediate of the length of the support, and preferably extends obliquely from the lower portion at about forty five degrees to the central axis of the lower portion. The upper portion preferably includes an extension portion extendable there from and both the upper portion and the extension portion are provided at their upper ends with attachment means for attaching intravenous fluid containers and the like thereto.

The base is preferably configured such that the front wheels can be accommodated underneath a bed. Preferably, the support can be clampingly engaged to a bed when it is desired to move the bed such that the mobility frame is moved with the bed.

The mobility frame preferably includes hooks or like means for supporting intravenous containers or electrical cords associated with the pumps or monitoring apparatus supported from the oblique portion at various positions thereon.

In another aspect, the present invention provides a mobility frame comprising:
   a multi-wheeled base,
   a pair of upstanding supports held in spaced relation to each other, each support having:

a substantially upright lower portion attached to the base, an oblique portion disposed at a height from the base, the oblique portion extending obliquely upwardly from the lower portion, an upper portion extending substantially upwardly from the oblique portion; and at least one handle for steering the mobility frame and/or for allowing a user to support them self on the mobility frame.

The base preferably includes two forwardly extending first arms and two generally rearwardly extending second arms which are divergent with respect to each other, each arm being supported on the ground by a wheel. Preferably, at least one of the first arms includes means for supporting a cylinder tank thereon. The lower portion of each support is preferably attached to one of the first arms and one of the second arms. The supports are preferably interconnected by at least one strut. A lower strut preferably connects the junction between the lower portion and the oblique portion and an upper strut connects between the upper ends of the upper portion. The supports are preferably interconnected by a third strut in the form of a metal plate and which is located at the lower end of the upper portions. The struts are preferably provided with suitable hooks or like means to support intravenous bags or electrical cords associated with pumps or monitoring apparatus supported from the oblique portion as required.

The mobility frame is preferably provided with a pair of handles, each handle extending from a lateral arm of each support, the handles extending in opposed relation to the oblique portion and spaced equi-distant to each side of a central axis of the frame. The handles are preferably adjustable in height.

Each lateral arm preferably has a vertical tubular portion with a clamp, each handle comprises a vertical portion slidingly received in the tubular portion and a horizontal portion having a grip, such that the height of the grips can be adjusted by moving the portions vertically relative to the lateral arms and then locking the desired grip height via the clamp. Preferably, a curved portion connects the vertical and horizontal portions of the handle. The handles preferably include forearm supports for supporting the user's forearms. The handle preferably includes an elongate horizontal concave portion which is padded at its top surface, the front end of the concave portion having a vertical grip.

The mobility frame is preferably configured such that it can be nested with another such mobility frame. Preferably, at various positions there along, the support includes hooks or like means for supporting intravenous containers or electrical cords associated with the pumps or monitoring apparatus supported from the oblique portion.

In another aspect, the present invention provides a mobility frame comprising:

a multi-wheeled base, a support attached to the base, the support having:

an oblique portion disposed at a height from the base for supporting monitoring equipment such that a user or person standing next to the frame can view the equipment;

an upper portion for supporting intravenous containers; and at least one handle for steering the mobility frame and/or for allowing a user to support them self on the mobility frame.

In another aspect, the present invention provides an intravenous support pole comprising:

a multi-wheeled base, and an upstanding support having:

a lower portion which is substantially aligned with the upright central axis of the base, an oblique portion substantially intermediate of the length of the support disposed at a height from the base, the oblique portion extending obliquely upwardly from the upper end of the lower portion, such that it presents its upper face towards the face of an intended user in use without the user having to change bodily position, and an upper portion extending upwardly from the upper end of the intermediate oblique portion.

Throughout the specification, unless the context requires otherwise, the word "comprise" or variations such as "comprises" or "comprising", will be understood to imply the inclusion of a stated integer or group of integers but not the exclusion of any other integer or group of integers.

The invention will be more fully understood in light of the following description of specific embodiment.

BRIEF DESCRIPTION OF THE DRAWINGS

The description is made with reference to the accompanying drawings:

FIG. 7a is a schematic front view of the first arms supporting a cylinder tank;

FIG. 7b is an enlarged view of the lower portion of FIG. 7a;

DETAILED DESCRIPTION OF SPECIFIC EMBODIMENTS

Each of the embodiments are directed to a mobility frame with medical apparatus support.

Figure 1:
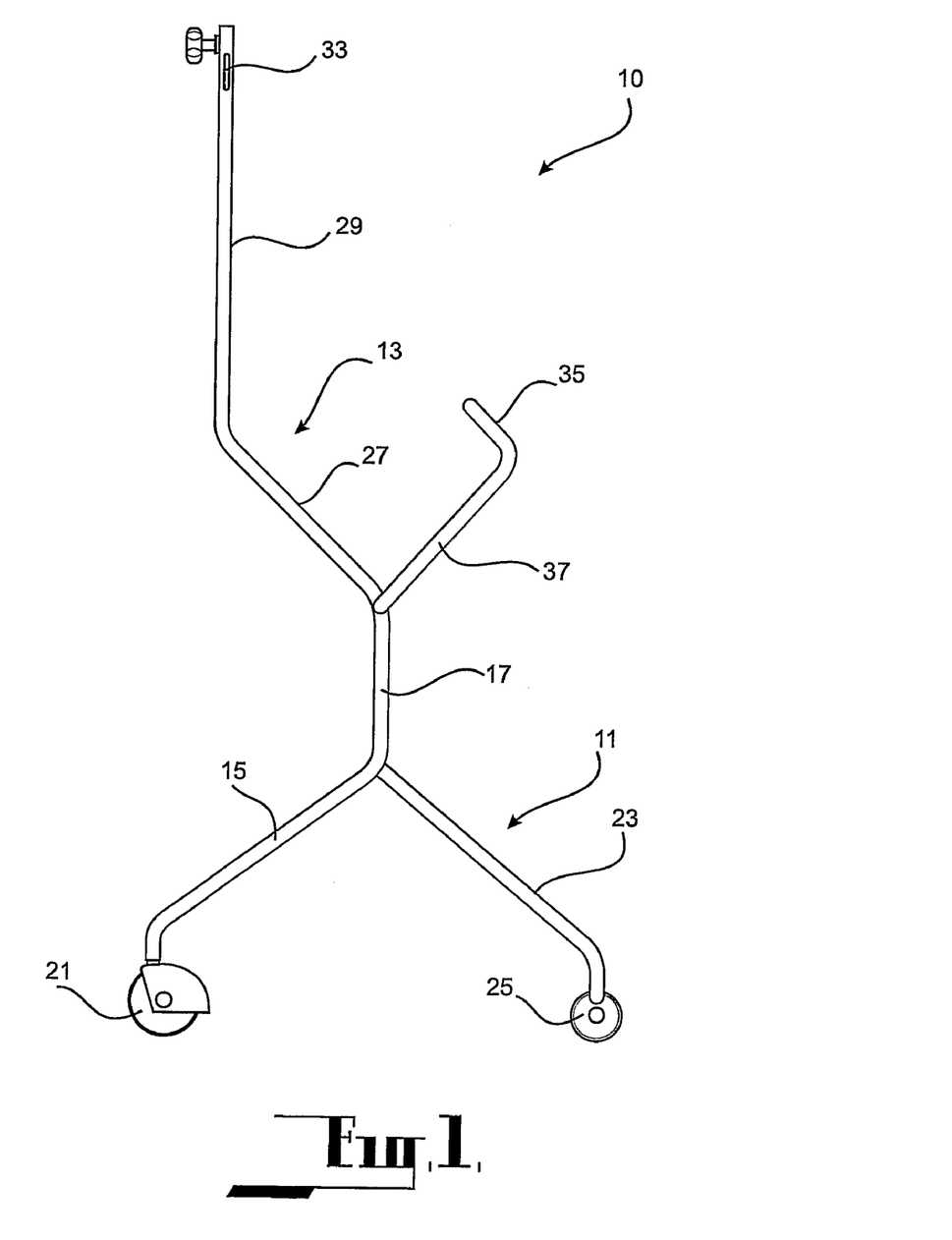
FIG. 1 is a side elevation of a mobility frame according to the first embodiment.
Figure 2:
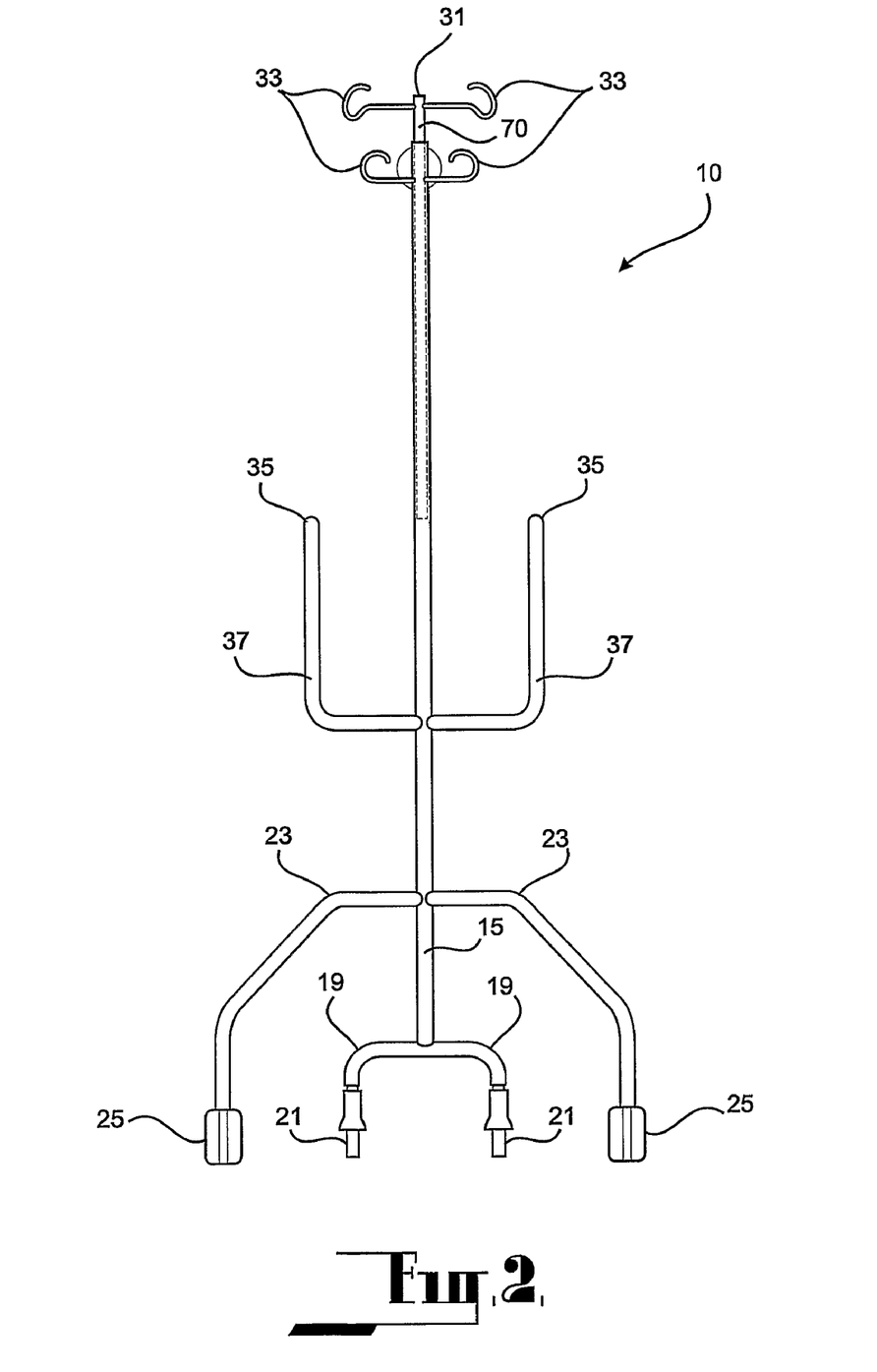
FIG. 2 is a rear elevation of a mobility frame according to the first embodiment.

In the case of the first embodiment the mobility frame 10 comprises a wheeled base 11 and a support 13. The support 13 comprises a lower portion 17 which is upright, an intermediate portion 27 which is obliquely upright and an upper portion 29 which is upright. The wheeled base 11 comprises a pair of first wheels 21 which are mounted to the lower end of a forwardly extending arm 15 which extends forwardly from the lower end of the lower portion 17 of the support 13. The lower end of the forwardly extending arm 15 is provided with a pair of lateral arms 19 which each support a first castor wheel 21 which are located equi-distant to each side of the forward arm 15. In addition, the wheeled base 11 comprises a pair of rear arms 23 which extend rearwardly from the lower portion 17 of the support 13 in opposed relation to the forward arm 15 but are in a divergent relationship to each other. Each of the rear arms 23 support a second castor wheel 25. The forward arm 15 and rear arms 23 are each downwardly divergent with respect to the central axis of the lower portion 17 of the support 13. The space in between the outer portions of the rear arms 23 and the second wheels 25 is sufficient to allow a person to stand adjacent the support 13. The forward arm 15 extends forwardly beyond the central axis of the upper portion 29 of the support 13 to provide the desired stability.

In addition, the support 13 is provided with a pair of handles 35 which are mounted at the outer end of a pair of laterally extending arms 37 whereby the arms 37 are in generally opposed relation to the oblique portion 27 and are located equi-distant to each side of the central axis. The handles 35 are located above the space defined between the rear wheels 25. The inner end portions of the laterally extending arms 37 can be provided with hooks or like means for supporting intravenous containers or electrical cords associated with the pumps or monitoring apparatus supported from the oblique portion 27 as described below.

The intermediate portion 27 of the support 13 extends obliquely from the upper end of the lower portion 17 at approximately forty five degrees to the central axis of the lower portion 17, and the upper end of the intermediate portion 27 is connected to the upper portion 29 which is generally upright. The upper portion 29 can be associated with an extension portion 31 and both the upper portion 29 and the extension portion 31 are provided at their upper ends with suitable support hooks 33 which can be used to engage intravenous fluid containers and the like.

In use it is intended that the oblique portion 27 will accommodate pumps and associated monitoring device which are required to be regularly observed by medical staff in relation to operating characteristics and performance of the devices. The oblique portion 27 is positioned and angled such that the display faces of such pumps and monitoring devices are readily seen by a person standing beside the mobility frame 10 and looking downwardly without the necessity for the person to bend over.

The intravenous mobility frame 10 according to the first embodiment enables intravenous fluid containers and the like to be supported from the support pole 10 in a conventional manner and the devices having a display which must be regularly observed and/or monitored can be located at a lower position on the pole 13.

It is envisaged that the intravenous mobility frame 10 according to the embodiment will provide significant advantages over existing intravenous support poles in that it will enable medical staff to readily monitor any equipment being carried upon the mobility frame 10 at the oblique intermediate portion 27 without having to bend over and without the centre of gravity of the loaded mobility frame 10 being unduly high. In addition, the provision of the handles 35 enables a person such as a patient to support themselves from the mobility frame 10 and to be able readily steer the frame 10. In addition, the base 11 is configured such that the front wheels 21 can be readily accommodated underneath a bed or alternatively can be located between a bed and bedside locker as required.

It is a further characteristic of the embodiment that the support 13 can be clampingly engaged to a bed when it is desired to move the bed such that it is moved with the bed.

Figure 3:
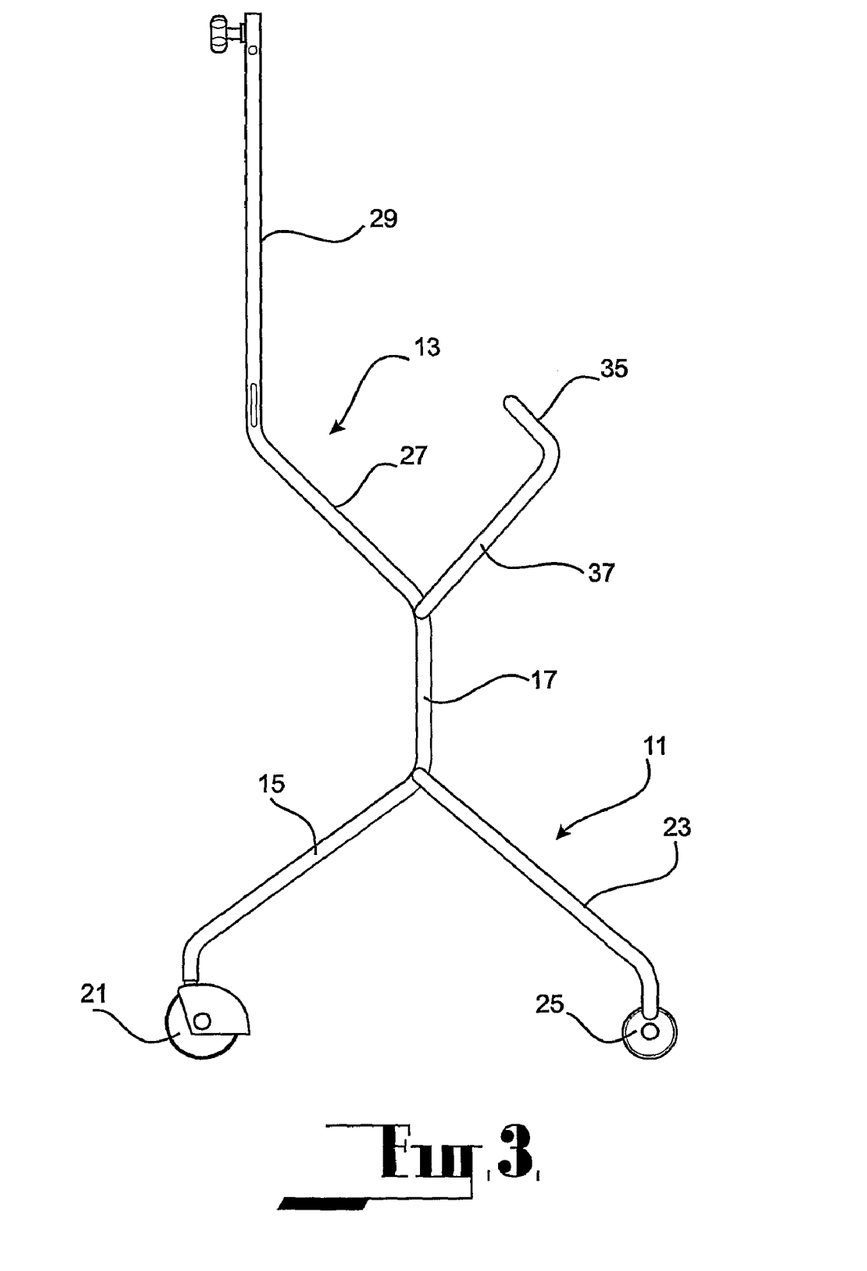
FIG. 3 is a side elevation of a mobility frame according to the second embodiment.
Figure 4:
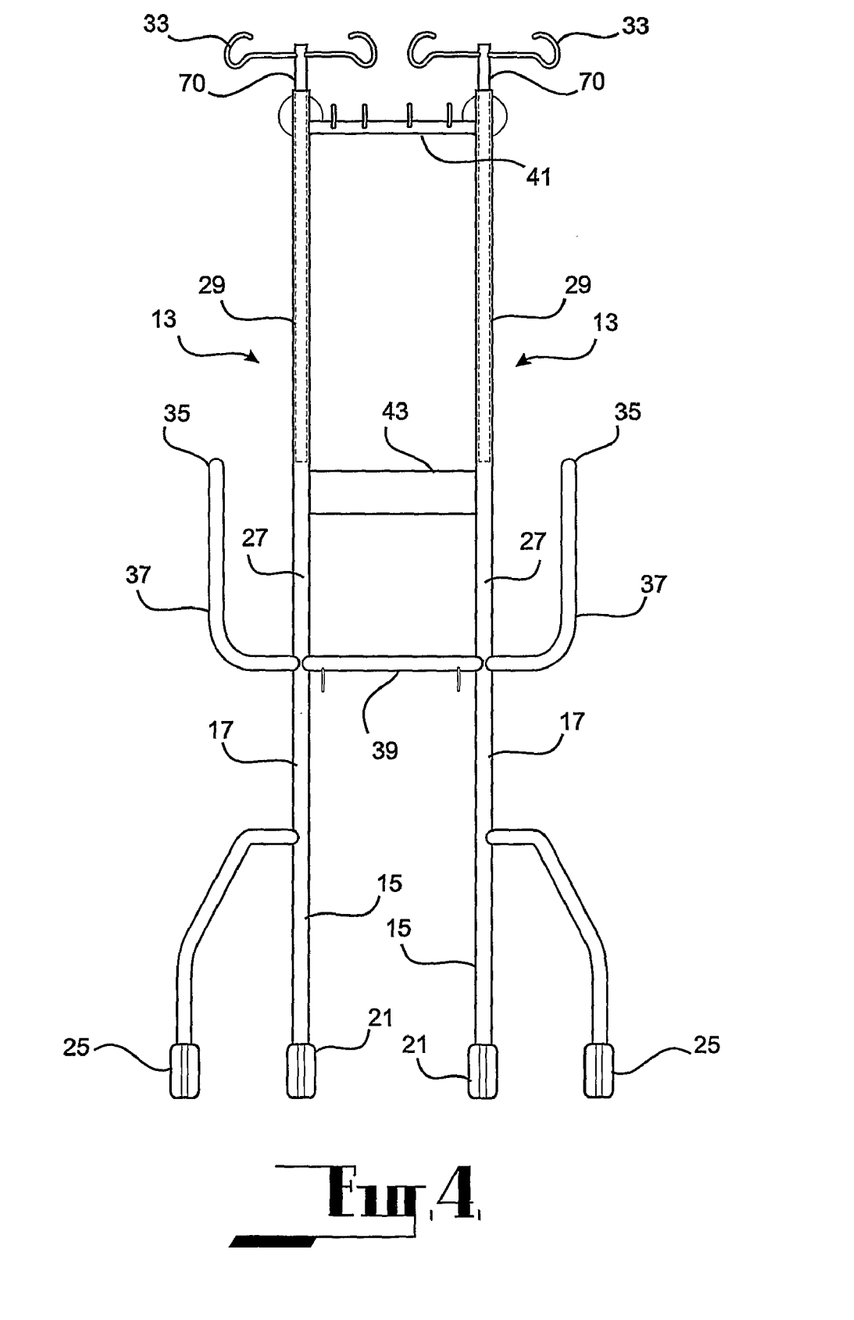
FIG. 4 is a rear elevation of a mobility frame according to the second embodiment.

The second embodiment as shown at FIGS. 3 and 4 is of generally the same form of that as the first embodiment and therefore the same numerals have been used in respect of corresponding components.

The principal difference between the first and second embodiments is that in the second embodiment there are a pair of upstanding supports 13 which are held in spaced relation to each other and where the lower portion 17 of each pole is associated with a forwardly extending arm 15, each having a first wheel 21 and each lower portion 17 supports one or the other of the second arms 23 which support the second wheels 25. The supports 13 are interconnected by a lower strut 39 located at the junction between the lower portion 17 and the oblique portion 27 and an upper strut 41 located between the upper ends of the upper portion 29. In addition, the supports 13 are interconnected by a third strut 43 which takes the form of a metal plate and which is located at the lower end of the upper portions 29. The first strut 39 and the second strut 41 may be provided with suitable hooks or like means to support intravenous bags for supporting intravenous containers or electrical cords associated with the pumps or monitoring apparatus supported from the oblique portion 27 as required. In addition each support 13 supports one of the handles 35 from the respective lateral arm 37.

The shape of the mobility frames 10, particularly the base 11 allows the frames 10 to be nested with other such frames 10 to minimize storage space. Also, the forward arms of the base 11 are typically configured which will allow same to be inserted underneath hospital beds when required.

Figures 5, 6:
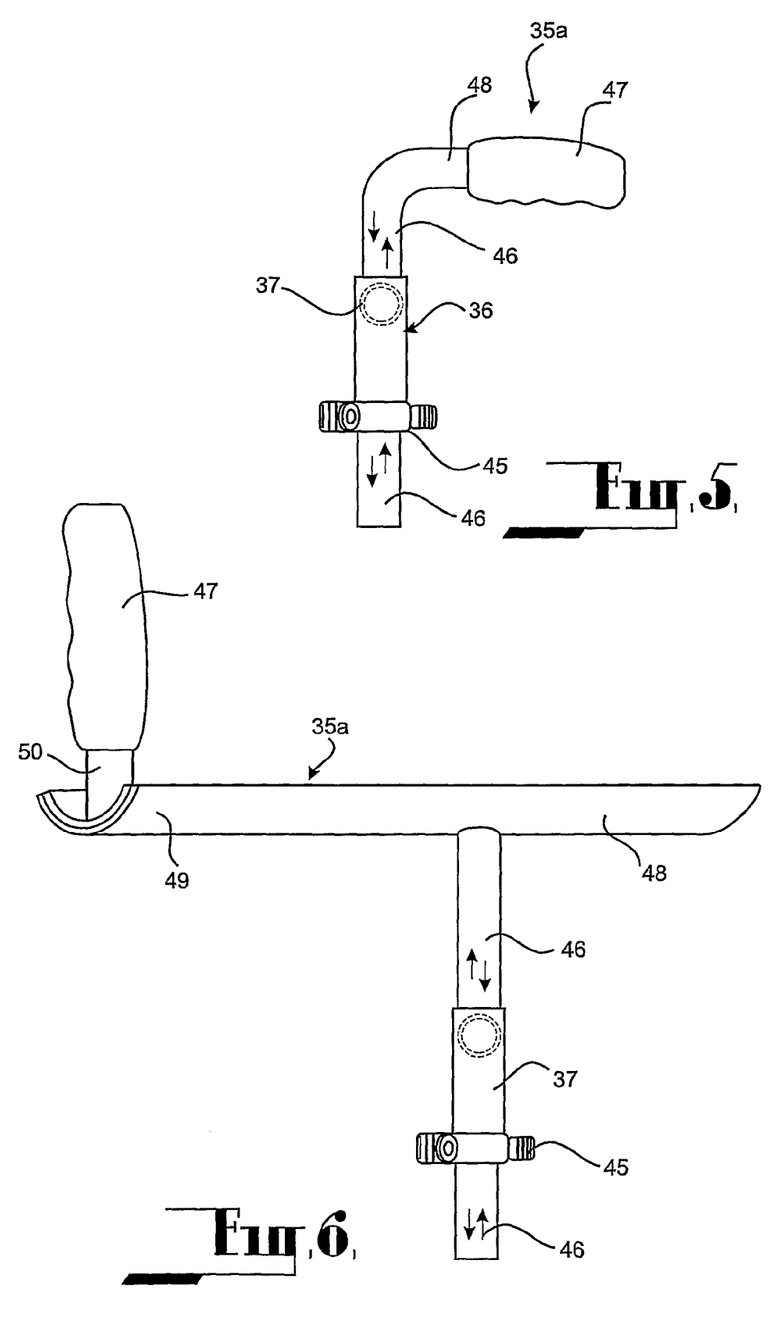
FIG. 5 is a schematic side view of an adjustable height handle for the mobility frame.
FIG. 6 is a schematic side view of an adjustable arm support for the mobility frame.

FIG. 5 shows a modification for the above embodiments, being an adjustable height handle 35a for the mobility frames. As shown, each lateral arm 37 has a vertical tubular portion 36 having a quick release clamp 45. Each handle 35a comprises a vertical portion 46 slidingly received in the tubular portion 36 and a horizontal portion 48 having a grip 47. The height of the grips 47 can thus be easily adjusted by moving the portions 46 vertically relative to the arms 37 and then locking the desired grip height via the clamps 45.

FIG. 6 shows a modification of FIG. 5, being an adjustable height forearm support 35a. As shown, the horizontal portion 48 is configured as an elongate concave portion. Padding is added to the top surface of the portion 48 and the front end 49 thereof is provided with a vertical grip shaft 50 and grip 47. In use, the user can rest his/her forearm in the horizontal portion 48 to support himself/herself.

Figures 7A, 7B:
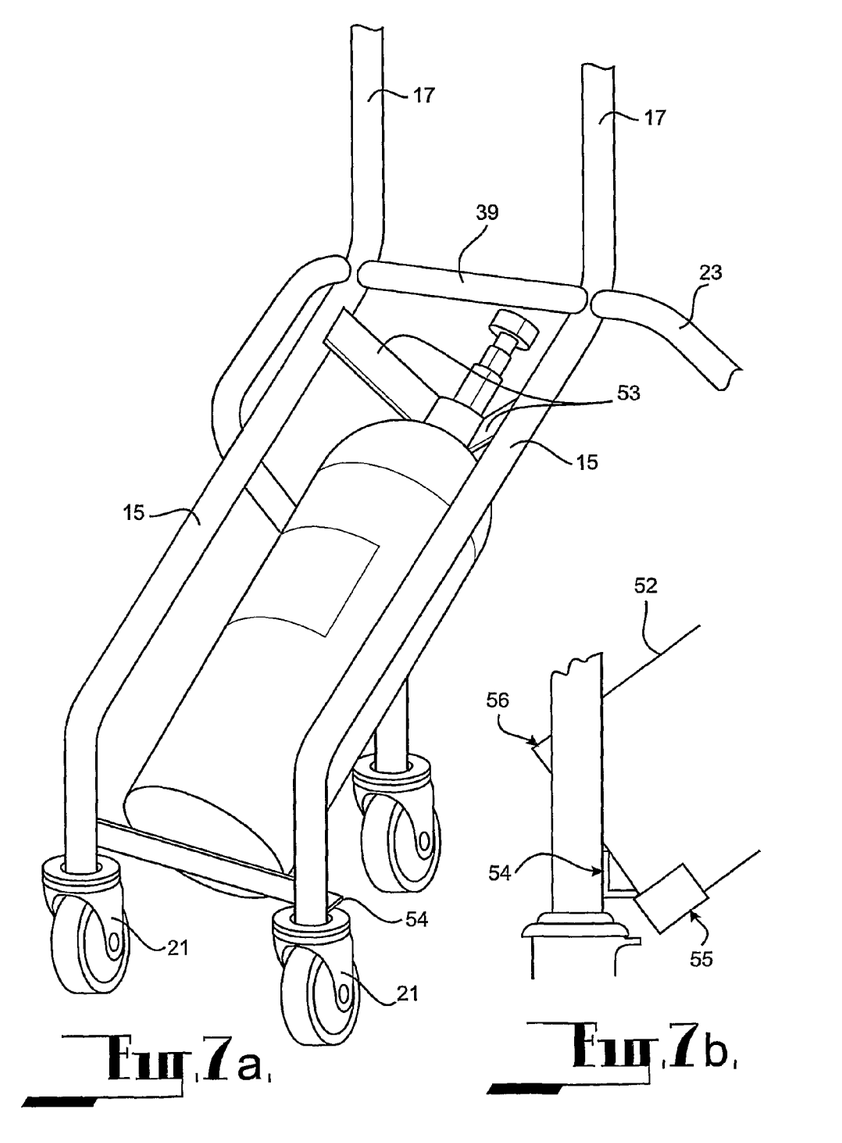
Figure 8A:
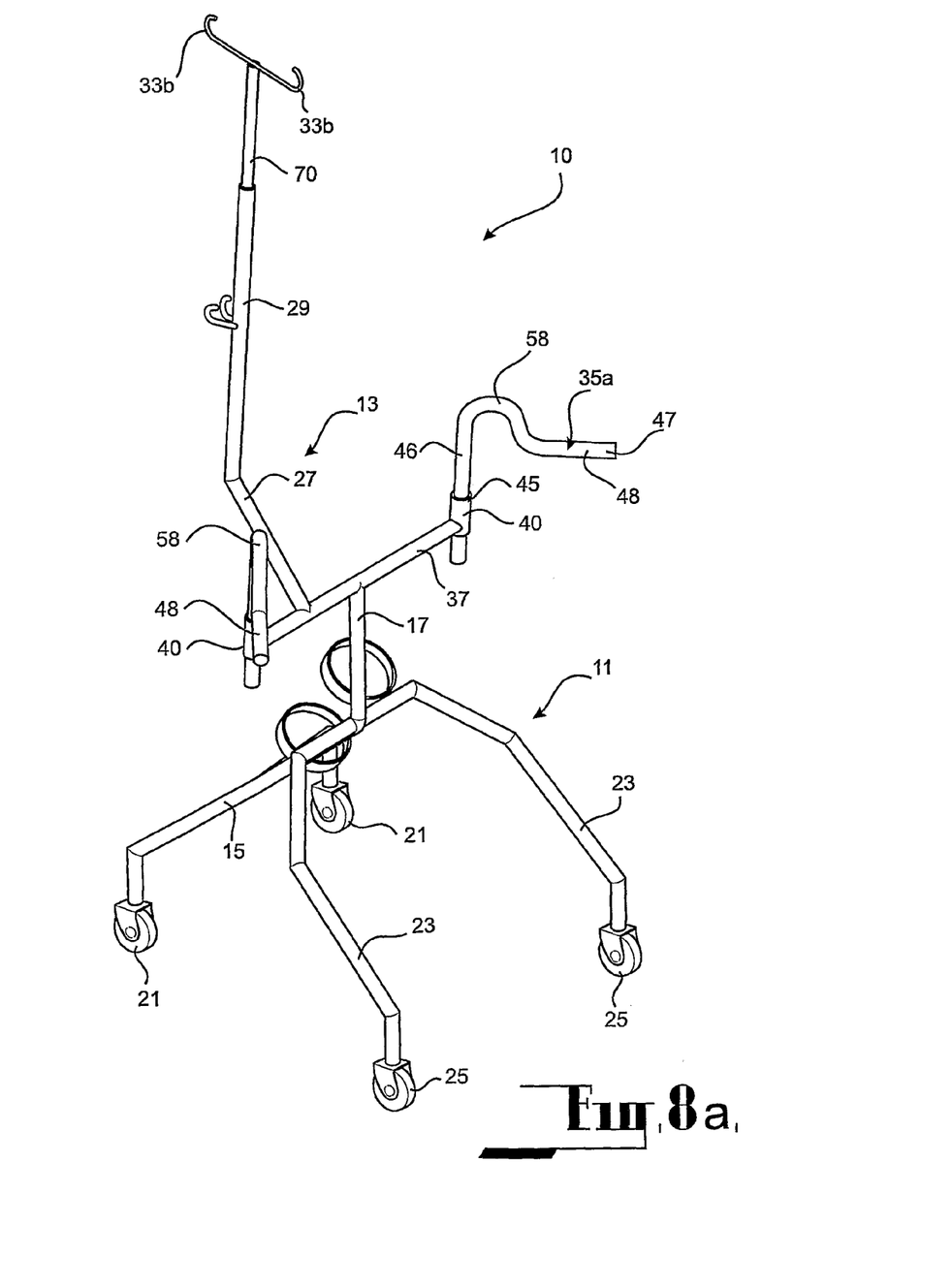
FIG. 8 is a mobility frame according to a modification of the first embodiment, where (a) shows a perspective view, (b) shows a front view, (c) shows a side view, and (d) shows a bottom view.
Figure 8B:
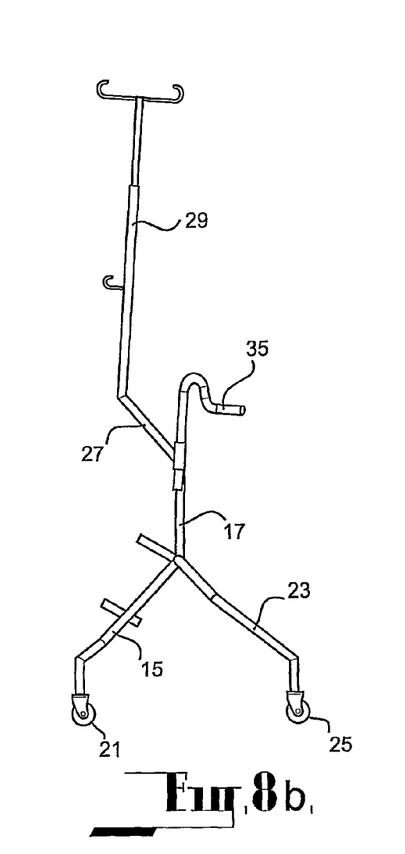
Figure 8C:
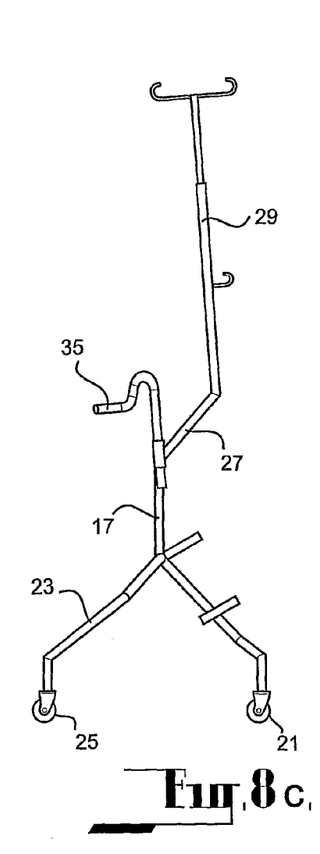
Figure 8D:
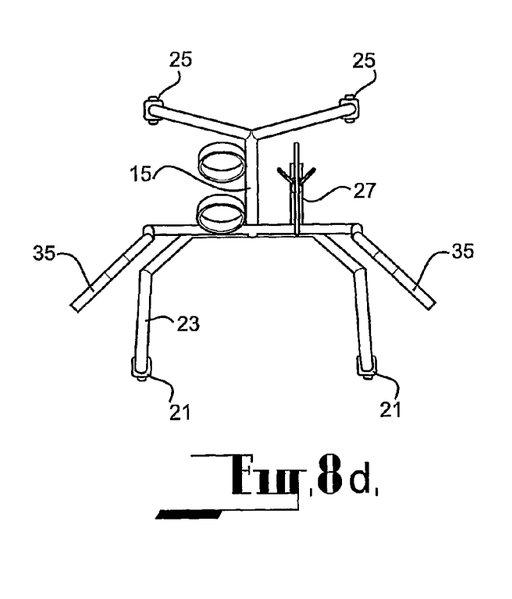

FIG. 7 shows the first arms 15 of the second embodiment supporting a cylinder tank 52. Angled plates 53 are attached to the arms 15 for supporting the neck of the tank 52. A foot brace 54 having a cup section 55 also extends between the lower portions of the arms 15. The foot brace 54 and cup section 55 support the base of the tank 52 with the front end 56 of the tank being located behind the front end 57 of the wheel castors 21. This substantially prevents the tank front end 57 from hitting walls.

In the case of each of the embodiments the lower portion 17 or the forward arm or second arms may support other ancillary elements apart from oxygen bottles or tanks which are required by the patient.

FIG. 8 shows a mobility frame according to a modification of the first embodiment. The modified embodiment as shown at FIG. 8 is of generally the same form of that as the first embodiment and therefore the same numerals have been used in respect of corresponding components. The principal differences between the first embodiment and the first modification is that in the first modified embodiment, the lower portion 17 of the support 13 is connected to the horizontal laterally extending arms 37. The oblique intermediate portion 27 is attached to a lateral arm 37 offset from the lower portion 17. The intermediate portion 27 and upper portion 29 are thus both located to a side of the central axis of the mobility frame 10 to substantially prevent same from blocking a user's forward direction view. The upper portion 29 is angled slightly in the rearward direction, typically by an angle of about 4° as shown, such that loads attached to hooks 33 of the upper portion 29 are located closer to the central axis of the mobility frame for stability. Also in the modified embodiment, the handles 35a are adjustable in height similar to that shown in FIG. 5. The lateral arms 37 include vertical tubular portions 40 having a quick release clamp 45. Each handle 35a comprises a vertical portion 46 slidingly received in the tubular portion 40, a horizontal portion 48 having a grip 47 and a curved portion 58 connecting the vertical and horizontal portions 46 and 48. The height of the grips 47 can thus be easily adjusted by moving the portions 46 vertically relative to the arms 37 and then locking the desired grip height via the clamps 45. The vertical portions 46 can also be inserted into the tubular portions 40 in the opposite direction to that shown (i.e. from the lower end of the tubular portions 40), such that the handles 48 will be located at a much lower height, for use of the mobility frame 10 by children or shorter persons. The curved portions 58 allow the handles 48 to be located substantially in line with the tubular portions 40. The forwardly extending arm 15 of the base 11 includes two rings for supporting a tank.

Figure 9A:
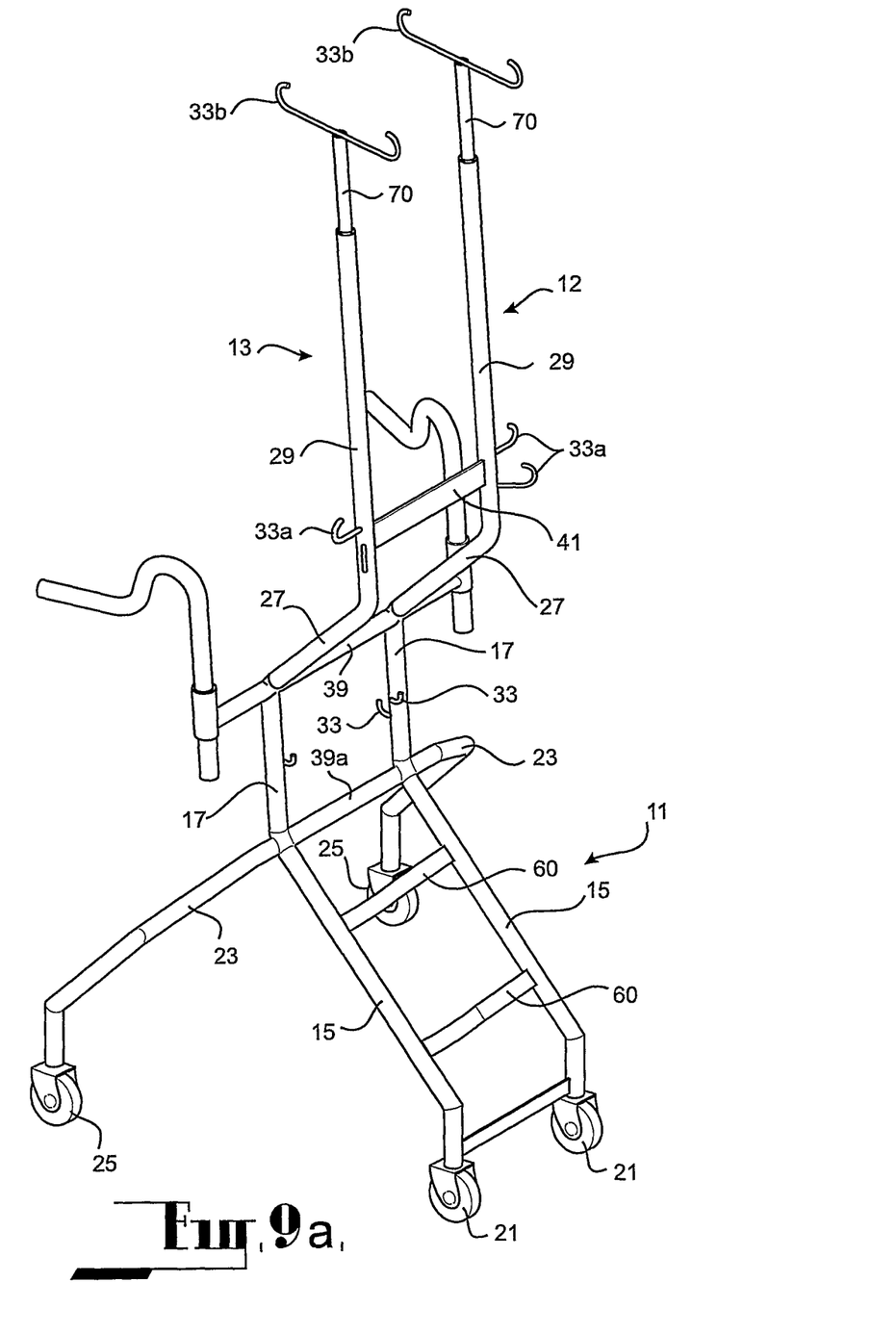
FIG. 9 is a mobility frame according to a modification of the second embodiment, where (a) shows a perspective view, (b) shows a left side view, (c) shows a right side view, and (d) shows a bottom view.
Figure 9B:
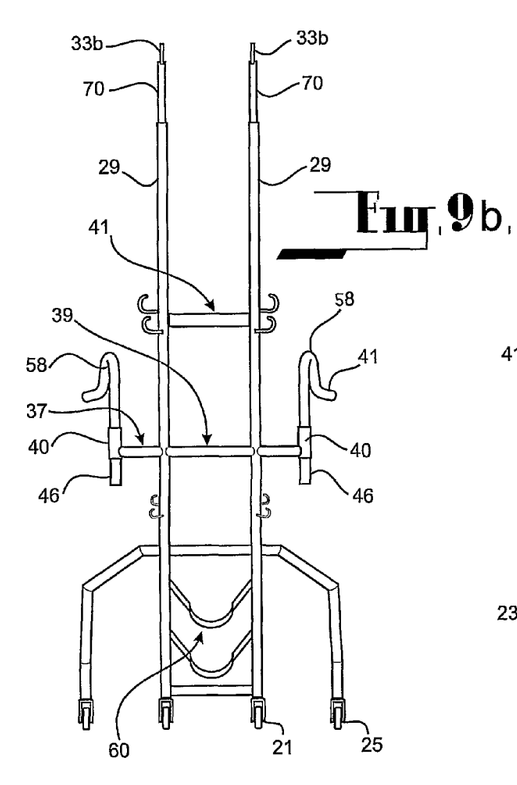
Figures 9C, 9D:
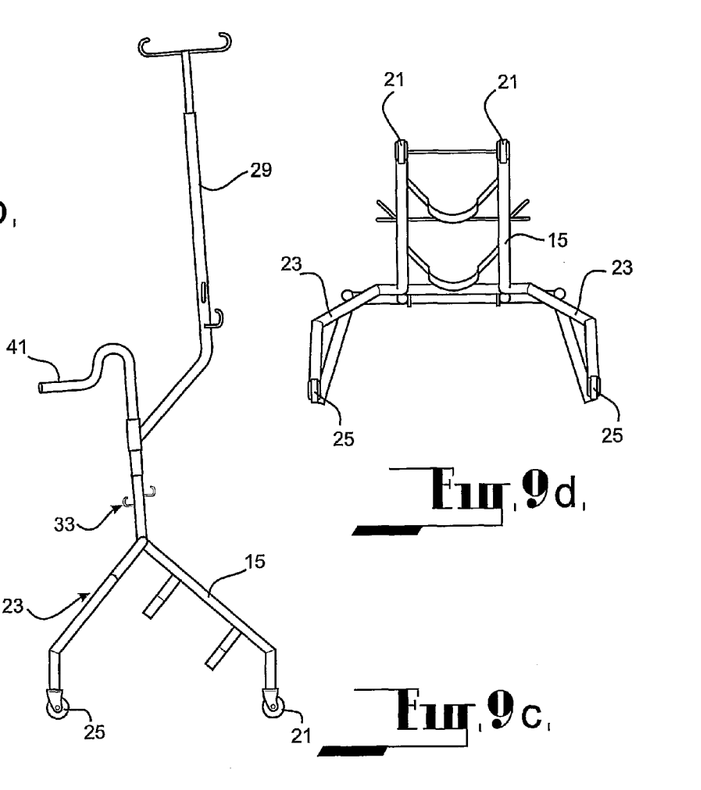

FIG. 9 shows a mobility frame according to a modification of the second embodiment which is of generally the same form of that as the second embodiment and therefore the same numerals have been used in respect of corresponding components. This second modification includes a pair of upstanding supports 13 which are held in spaced relation to each other and where the lower portion 17 of each pole is associated with a forwardly extending arm 15, each having a first wheel 21 and each lower portion 17 supports one of the second arms 23 which support the second wheels 25. The supports 13 are interconnected by a middle strut 39 located at the junction between the lower portion 17 and the oblique portion 27, a lower strut 39a at the lower ends of the lower portions 17 and an upper strut 41 located between the upper portions 29 which takes the form of a metal plate and which is located at the lower end of the upper portions 29. Suitable hooks 33 or like means are provided at various positions of the mobility frame to support intravenous bags for supporting intravenous containers or electrical cords associated with the pumps or monitoring apparatus supported from the oblique portion 27 as required. In addition each support 13 supports one of the adjustable height handles 35a from a respective lateral arm 37 similar to that shown in FIG. 8. The base 11 includes two forwardly extending arms 15 which are in opposed relation to the rear arms 23. The forward arms 15 are parallel to each other and include two spaced curved cradles 60 for supporting a cylinder tank thereon. This modification also includes four fixed height hooks 33a for pumped fluid which do not need to be raised to gravity feed height.

Each of the modifications described includes extension poles 70 slidably inserted into the support upper portions 29. The extension poles 70 include hooks 33b the height of which is adjustable by moving the poles 70 along the upper portions 29. Various other devices and items can be attached to the mobility frames, such as sealed drain bottles clipped to an arm of the base, baskets and nets, and hand brakes can also be attached to the rear/front wheels. Further support plates can be attached to the support 13 for attachment of devices as required, particularly at the oblique portion 27.

It should be appreciated that the scope of the present invention need not be limited to the particular scope of the embodiment described above.

The claims defining the invention are as follows:

1. A mobility frame comprising:
   a multi-wheeled base;
   an upstanding support having:
      a substantially upright lower portion attached to the base,
      a substantially horizontal arm attached to the upright lower portion,
      an oblique portion attached to the horizontal arm and offset from the lower portion, the oblique portion extending obliquely upwardly from the horizontal arm, and
      an upper portion extending substantially upwardly from the oblique portion;
   tubular portions positioned at each end of the horizontal arm; and
   handles respectively connected to each tubular portion, each handle being adjustable in a vertical direction within the tubular portions and structured for steering the mobility frame and/or for allowing a user to support them self on the mobility frame,
   wherein the oblique portion is adapted to support a medical apparatus.

2. The mobility frame of claim 1 wherein the lower portion is substantially aligned with the upright central axis of the base.

3. The mobility frame of claim 1 wherein the height of the oblique portion is such that monitoring devices attached thereto can be viewed by a user or carer standing next to the mobility frame.

4. The mobility frame of claim 1 wherein the upper portion is angled in the rearward direction such that loads attached to the upper portion are located closer to a central axis of the mobility frame.

5. The mobility frame of claim 1 wherein the base is defined by a first arm extending radially from the upstanding support and a pair of second arms which are in an opposed relation to the first arm and divergent with respect to each other, the first arm and second arms each being supported from the ground by a wheel.

6. The mobility frame of claim 5 wherein the spacing between the wheels of the second arms is sufficient to enable a person to engage the handle(s) and stand between the second arms.

7. The mobility frame of claim 5 wherein the first arm extends forwardly beyond a central axis of the upper portion of the support to provide stability.

8. The mobility frame of claim 5 wherein the first and second arms are divergently downwardly with respect to a central axis of the lower portion.

9. The mobility frame of claim 5 wherein the base includes two first arms which are in opposed relation to the second arms, the first arms each being supported from the ground by a wheel.

10. The mobility frame of claim 9 wherein the first arms are parallel to each other.

11. The mobility frame of claim 10 wherein at least one first arm includes a means for supporting a cylinder tank thereon.

12. The mobility frame of claim 1 wherein the vertical adjustment of the handles adjusts a height of the handles relative to a surface that the base is positioned on.

13. The mobility frame of claim 12 wherein each vertical tubular portion with a clamp, each handle comprises a vertical portion slidingly received in the tubular portion and a horizontal portion having a grip, such that the height of the grips can be adjusted by moving the vertical portions vertically relative to the lateral arms and then locking the desired grip height via the clamp.

14. The mobility frame of claim 13 wherein a curved portion connects the vertical and horizontal portions of the grip.

15. The mobility frame of claim 1 wherein the handles include forearm supports for supporting the user's forearms.

16. The mobility frame of claim 15 wherein the handle includes an elongate horizontal concave portion which is padded at its top surface, the front end of the concave portion having a vertical grip.

17. The mobility frame of claim 1 wherein the base is defined by a first arm extending radially from the upstanding support and a pair of second arms which are in an opposed relation to the first arm and divergent with respect to each other, the first arm and second arms each being supported from the ground by a wheel, the spacing between the wheels of the second arms is sufficient to enable a person to engage the handles and stand between the second arms, and the handles are located above the space defined between the wheels of the second arms.

18. The mobility frame of claim 1 wherein the oblique portion extends from the upper end of the lower portion.

19. The mobility frame of claim 1 wherein the upper portion extends from the upper end of the oblique portion.

20. The mobility frame of claim 1 wherein the oblique portion is substantially intermediate of the length of the support.

21. The mobility frame of claim 1 wherein the oblique portion of the support extends obliquely from the lower portion at about forty five degrees to the central axis of the lower portion.

22. The mobility frame of claim 1 wherein the upper portion includes an extension portion extendable therefrom and both the upper portion and the extension portion are provided at their upper ends with attachment means for attaching intravenous fluid containers and the like thereto.

23. The mobility frame of claim 1 wherein the base is configured such that the front wheels can be accommodated underneath a bed.

24. The mobility frame of claim 1 wherein the support can be clampingly engaged to a bed when it is desired to move the bed such that the mobility frame is moved with the bed.

25. The mobility frame of claim 1 wherein the support includes hooks or like means for supporting intravenous containers or electrical cords associated with the pumps or monitoring apparatus supported from the oblique portion at various positions thereon.

* * * * *